US007499866B2

(12) United States Patent
Summers et al.

(10) Patent No.: US 7,499,866 B2
(45) Date of Patent: Mar. 3, 2009

(54) METHOD FOR DIRECT-TO-PATIENT MARKETING AND CLINICAL TRIALS RECRUITMENT WITH OUTCOMES TRACKING AND METHOD FOR CONFIDENTIAL APPOINTMENT BOOKING

(75) Inventors: Mark Summers, Orono, MN (US); Jennifer Mary Zwiefel Renaud, Greenwood, MN (US); Gary Russell Lindberg, Chanhassen, MN (US)

(73) Assignee: ThreeWire, Inc., Eden Prairie, MN (US)

( * ) Notice: Subject to any disclaimer, the term of this patent is extended or adjusted under 35 U.S.C. 154(b) by 1163 days.

(21) Appl. No.: 10/440,594

(22) Filed: May 19, 2003

(65) Prior Publication Data

US 2004/0236601 A1 Nov. 25, 2004

(51) Int. Cl.
G06Q 10/00 (2006.01)
(52) U.S. Cl. ................. 705/2; 705/3; 705/4; 600/300
(58) Field of Classification Search .............. 705/2–4
See application file for complete search history.

(56) References Cited

U.S. PATENT DOCUMENTS

| | | | | | |
|---|---|---|---|---|---|
| 5,737,539 | A | * | 4/1998 | Edelson et al. ............. | 705/3 |
| 5,845,255 | A | * | 12/1998 | Mayaud ..................... | 705/3 |
| 5,911,687 | A | * | 6/1999 | Sato et al. ................. | 600/300 |
| 6,018,713 | A | * | 1/2000 | Coli et al. .................. | 705/2 |
| 6,223,165 | B1 | * | 4/2001 | Lauffer ...................... | 705/8 |
| 6,256,613 | B1 | * | 7/2001 | Falchuk et al. ............. | 705/2 |
| 6,283,761 | B1 | * | 9/2001 | Joao ......................... | 434/236 |
| 6,389,454 | B1 | * | 5/2002 | Ralston et al. ............. | 709/204 |
| 6,697,783 | B1 | * | 2/2004 | Brinkman et al. ........... | 705/3 |
| 6,757,898 | B1 | * | 6/2004 | Ilsen et al. ................. | 709/203 |
| 2001/0021910 | A1 | * | 9/2001 | Goldstein ................... | 705/2 |
| 2001/0023419 | A1 | * | 9/2001 | Lapointe et al. ............ | 706/15 |
| 2002/0002474 | A1 | * | 1/2002 | Michelson et al. .......... | 705/3 |
| 2002/0019746 | A1 | * | 2/2002 | Rienhoff et al. ............ | 705/2 |
| 2002/0032581 | A1 | * | 3/2002 | Reitberg .................... | 705/2 |
| 2002/0042723 | A1 | * | 4/2002 | Rice et al. .................. | 705/2 |
| 2002/0082464 | A1 | * | 6/2002 | Japp et al. .................. | 600/10 |
| 2002/0165732 | A1 | * | 11/2002 | Ezzeddine et al. .......... | 705/2 |
| 2003/0149595 | A1 | * | 8/2003 | Murphy ..................... | 705/2 |
| 2003/0208378 | A1 | * | 11/2003 | Thangaraj et al. .......... | 705/2 |
| 2004/0078216 | A1 | * | 4/2004 | Toto .......................... | 705/2 |
| 2004/0199412 | A1 | * | 10/2004 | McCauley .................. | 705/7 |

* cited by examiner

*Primary Examiner*—Gerald J. O'Connor
*Assistant Examiner*—Vivek D Koppikar
(74) *Attorney, Agent, or Firm*—Altera Law Group, LLC

(57) ABSTRACT

Generally, the present invention is directed to marketing techniques and more particularly to direct-to-patient marketing for medical devices, pharmaceutical drugs, and biotechnology products. The approach presented here may also be applied to the recruitment of patients for clinical trials evaluation including tracking outcomes after treatment. An embodiment of the invention includes the steps of finding potential patients, qualifying potential patients, connecting potential patients to preferred physicians, and tracking the patient's progress through the appointment phase and tracking outcomes.

25 Claims, 20 Drawing Sheets

METHOD FOR DIRECT-TO-PATIENT MARKETING AND CLINICAL TRIALS RECRUITMENT WITH OUTCOMES TRACKING AND METHOD FOR CONFIDENTIAL APPOINTMENT BOOKING

FIELD OF THE INVENTION

The present invention is directed generally to marketing techniques and more particularly to direct-to-patient marketing for medical devices, pharmaceutical drugs, and biotechnology products. The approach presented here may also be applied to the recruitment of patients for clinical trials evaluation including tracking outcomes after treatment. The approach presented here may also be applied to a wide variety of consumer products such as automotive parts, electronic components, and the like.

BACKGROUND

For over fifty years, medical device companies (along with pharmaceutical and biotechnology firms) have been marketing and selling their products in a conventional Value-Added Reseller (VAR) model. Physicians who become users of a given product act as value-added resellers to patients or third-party payers such as insurance companies and HMOs.

Unfortunately, the slow pace of recruiting significant numbers of physicians often throttles product sales because the only patients who can be sold the product are those who have contact with the limited number of physicians who use/endorse the product. This leaves the vast majority of potential patients untapped. This problem is particularly problematic for start-up or emerging phase medical device firms with a limited sales and marketing staff and/or budget to reach the geographically dispersed physician population.

Another area within the medical community sensitive to similar constraints lies in the recruitment and tracking of patients in a clinical trials setting. Here, the problem is at least three-fold. First, especially in the case of therapeutic drugs, a sufficiently large patient population needs to be identified and recruited with a specific disease state or condition appropriate for the drug under evaluation. Secondly, the recruited patient population needs to be tracked through the clinical treatment protocol, where in many cases multiple procedures are required over extended periods of time. And lastly, in many cases the outcomes evaluation of the therapeutic drug or procedure may require extended tracking of the patient population after treatment has been completed to quantify long-term benefits (e.g., survival rates) and uncover unexpected side-effects.

Given the above scenario, there is a need for a method of finding and pre-screening (qualifying) potential patients either for referral to an appropriate physician or clinical trials investigator, with the follow-on goal of tracking their progress through the various stages of appointment, treatment, and outcomes verification.

SUMMARY OF THE INVENTION

Generally, the present invention relates to marketing techniques and more particularly to direct-to-patient marketing for medical devices, pharmaceutical drugs, and biotechnology products. The approach presented here may also be applied to a wide variety of consumer products such as automotive parts, electronic components, and the like.

One particular embodiment of the invention is directed to finding potential patients who are candidates for a specific product. The method also includes the steps of qualifying the potential patients utilizing a pre-determined criterion, connecting qualified patients to a vendor providing the specific product, and tracking patient satisfaction.

Another embodiment of the present invention is directed to a method of booking and tracking secure patient appointments with a preferred physician. The method also includes the steps of employing an on-line secure, password protected portal for communication between the booking agent and the preferred physician. The marketing company may also contract with the preferred physician for pre-approved appointment time slots, which may be scheduled by the booking agent. The booking agent may confirm that the patient made the scheduled appointment and track outcomes by querying the preferred physician by means of the secure portal.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
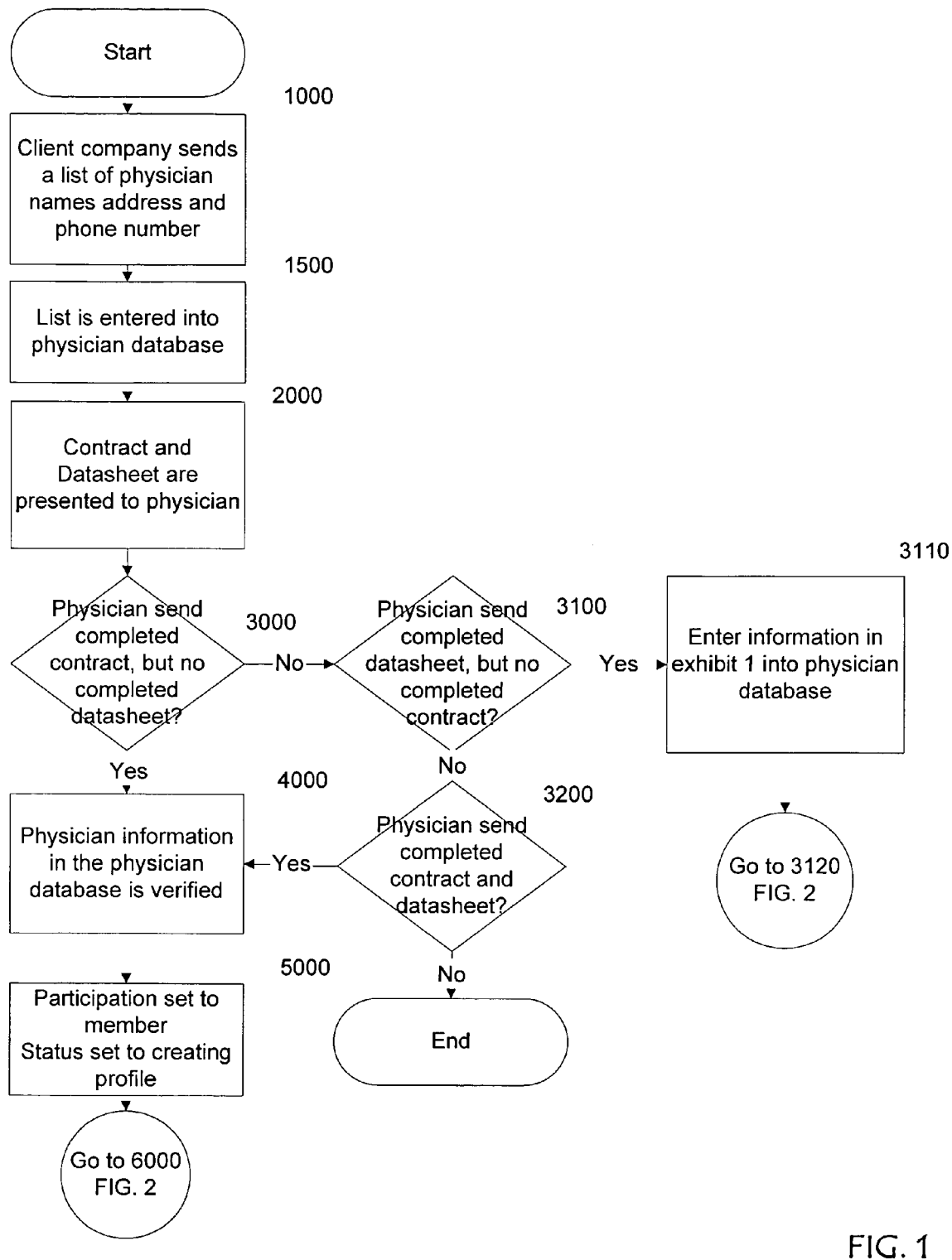
FIG. 1 through FIG. 18 and the accompanying exhibits 1 through 4 outline the process of finding, qualifying, connecting, and tracking potential patients/patients in flowchart format.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

In general, the present invention is directed to marketing techniques and more particularly to direct-to-patient marketing for medical devices, pharmaceutical drugs, and biotechnology products. The approach presented here may also be applied to a wide variety of consumer products such as automotive parts, electronic components, and the like.

In one embodiment of the present invention the web-based direct-to-patient marketing technique is designed to accomplish at least four goals, they are:

1) Find patients who are candidates for a specific medical product or therapy;
2) Qualify the potential patients per a pre-determined criterion;
3) Connect qualified patients to a physician using a pre-determined product or therapy;
4) Track patients through the appointment visit and treatment phase and track outcomes.

An embodiment of the process of finding, qualifying, connecting, and tracking potential patients is outlined below in flowchart format as described in FIGS. 1 through FIG. 18 and the accompanying exhibits 1 through 4.

In one embodiment the process may be a direct-to-patient marketing program funded by a client company with their own particular device or procedure, wherein the client company has an already established physician and/or health care professional base which utilizes or prescribes the client company's product. Wherein health care professionals may include doctors, dentists, nurses or non-licensed agents of the marketing company. In order to recruit potential patients to physicians and/or health care professionals who use the client company's products (hereafter referred to as preferred physicians), the marketing company may establish and maintain a non-branded informational website to attract patients with a specific medical condition relevant to the client company's products. This non-branded website may contain non-branded medical information about the relevant medical condition and may also include a toll-free number where interested parties may speak directly with an agent of the marketing company at a facility hereafter referred to as the Patient Interaction Center (PIC). The agents at the Patient Interaction Center may be health care professionals (nurses, med-techs, physicians, etc.) who may answer general medical questions posed by callers. The PIC agents may also screen (qualify) potential patients by asking a series of questions designed to determine if the caller is a good candidate for the client company's products. The qualifying questions may include, but are not limited to, determining the following;

1) verifying that specific alternative medical options for treating the patient's medical condition have been tried and failed.
2) verifying that specific alternative medical options for treating the patient's medical condition have been evaluated and rejected.
3) verifying that the potential patient may not have adverse reactions to certain drugs or techniques that may be used with the client's specific medical product or procedure.
4) verifying that the potential patient has medical insurance or alternative means to pay for the client's specific medical product or procedure.

The PIC agents may also have the ability to refer potential patients to the client's preferred physicians, as well as book an appointment with a preferred physician.

The marketing company may also generate and maintain a database to track a patient through the entire process of scheduling an appointment, reminding the patient of the upcoming appointment, re-scheduling the appointment if necessary, and providing a secure, or password protected, portal entry into the database for the preferred physician to record outcomes.

Figure 2:
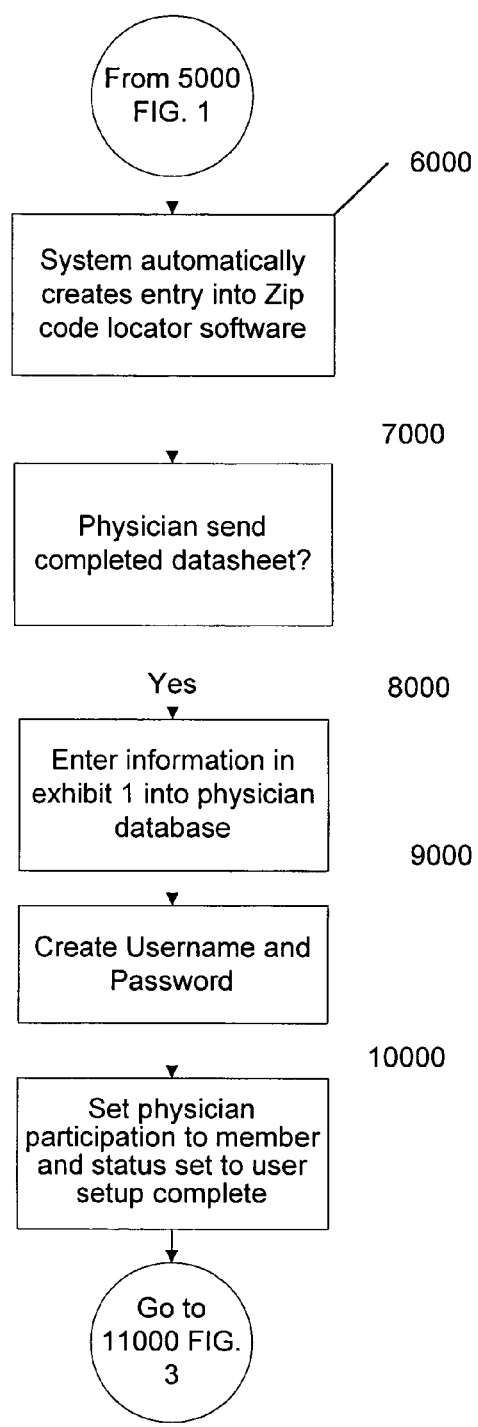

With reference to FIG. 1, the process starts wherein the client company may provide a list of its preferred physicians (FIG. 1; step 1000) to the marketing company which in turn may enter this information into a physician database (FIG. 1; step 1500). The marketing company may then forward a contract and datasheet (exhibit 1) to the preferred physician (FIG. 1; step 2000). If the physician chooses to participate in the program by completing the enrollment contract (FIG. 1; step 3000), the marketing company verifies the information is correct in the physician database (FIG. 1; step 4000) and the physician may then be designated as a participating member (FIG. 1; step 5000), and the physician may be entered into a software package which locates physicians near a particular postal (zip) code (FIG. 2; step 6000). Once the physician completes and forwards the datasheet (FIG. 1; steps 3100 through 3200) to the marketing company (FIG. 2; step 7000), the information may be entered into the marketing company's physician database (FIG. 2; step 8000) and a Username and Password may be created for the physician (FIG. 2; step 9000) to enter the database via a secure portal operated by the marketing company, and the physician is designated as a participating member with set-up complete (FIG. 2; step 10000).

Figure 3:
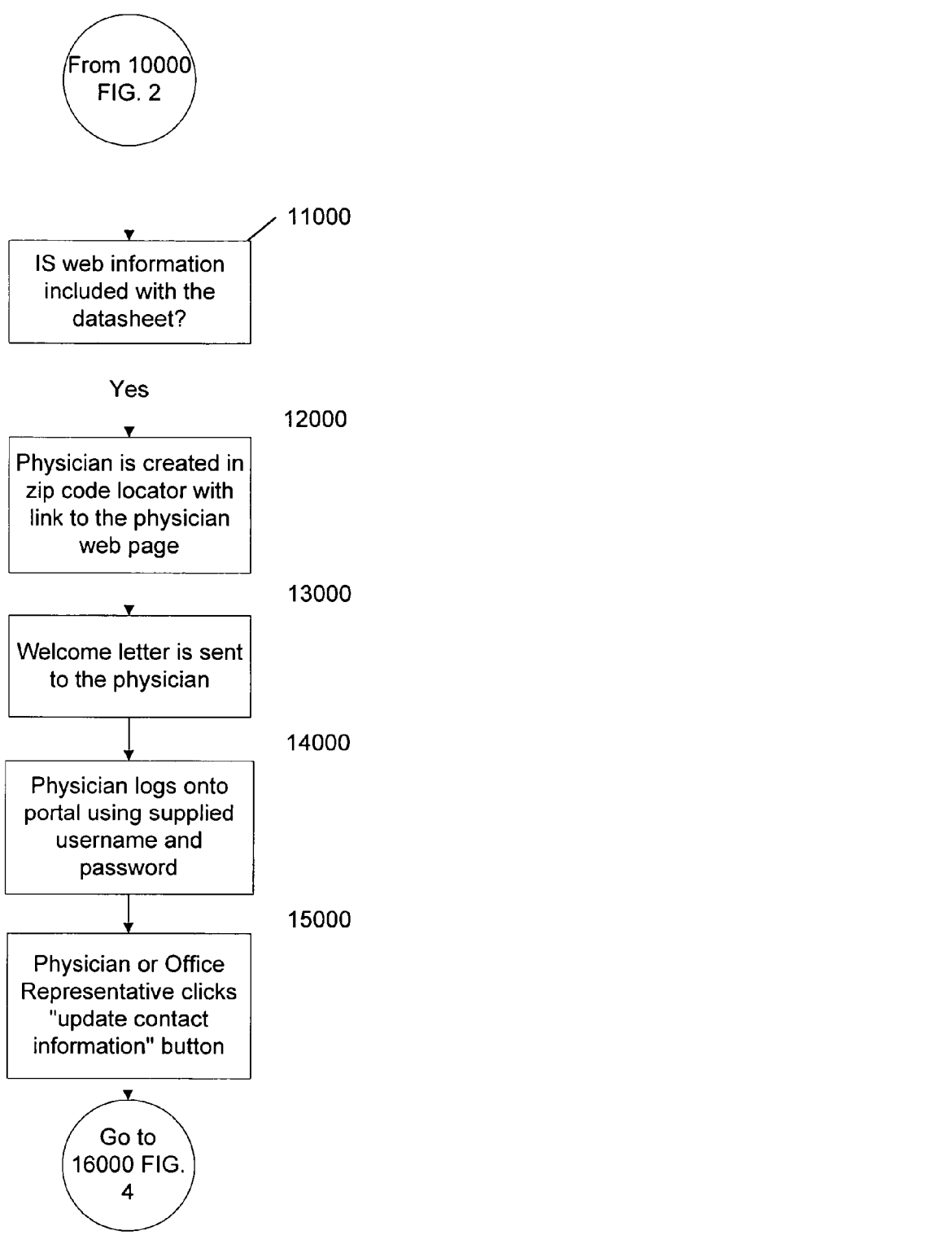
Figure 4:
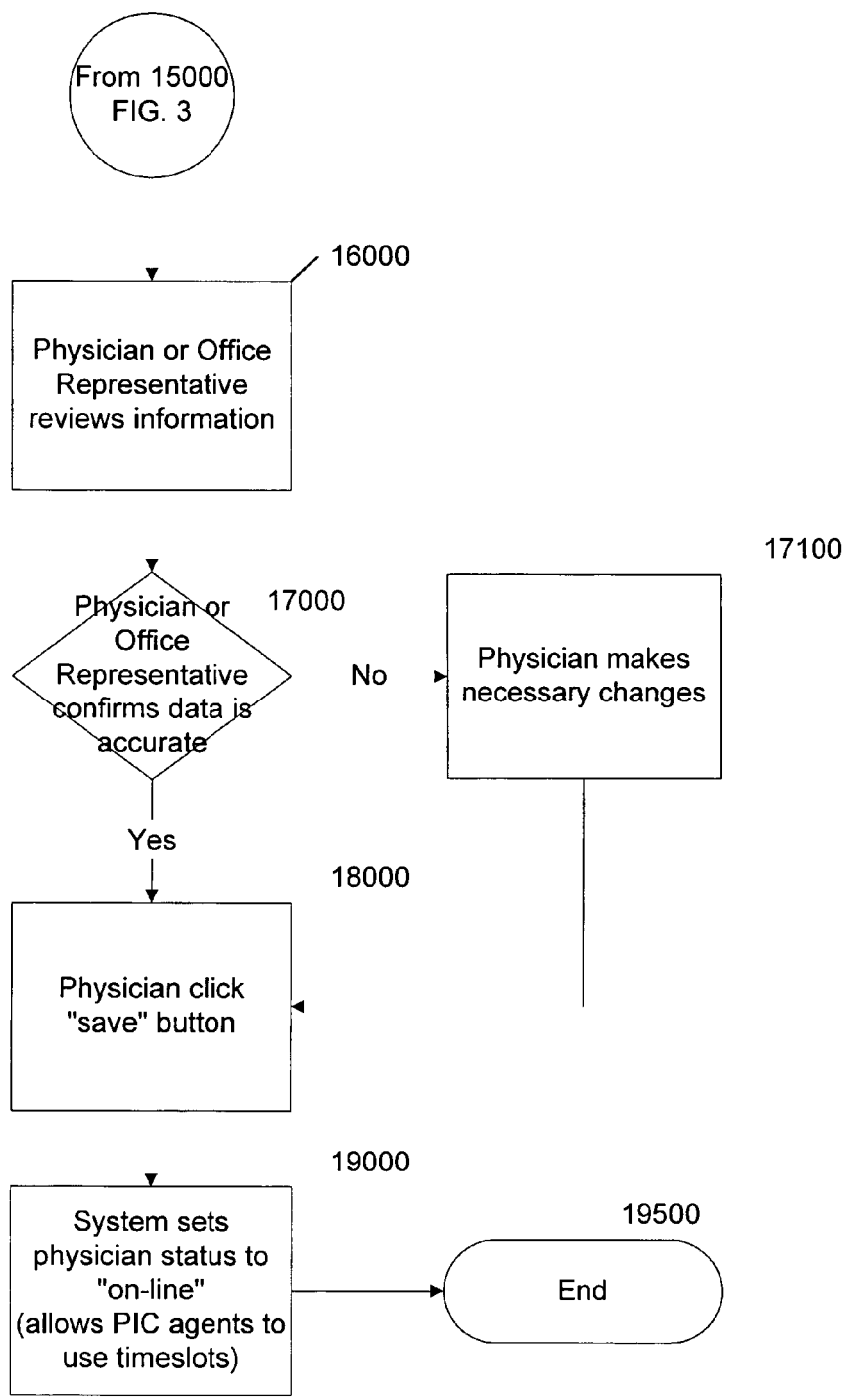
Figure 5:
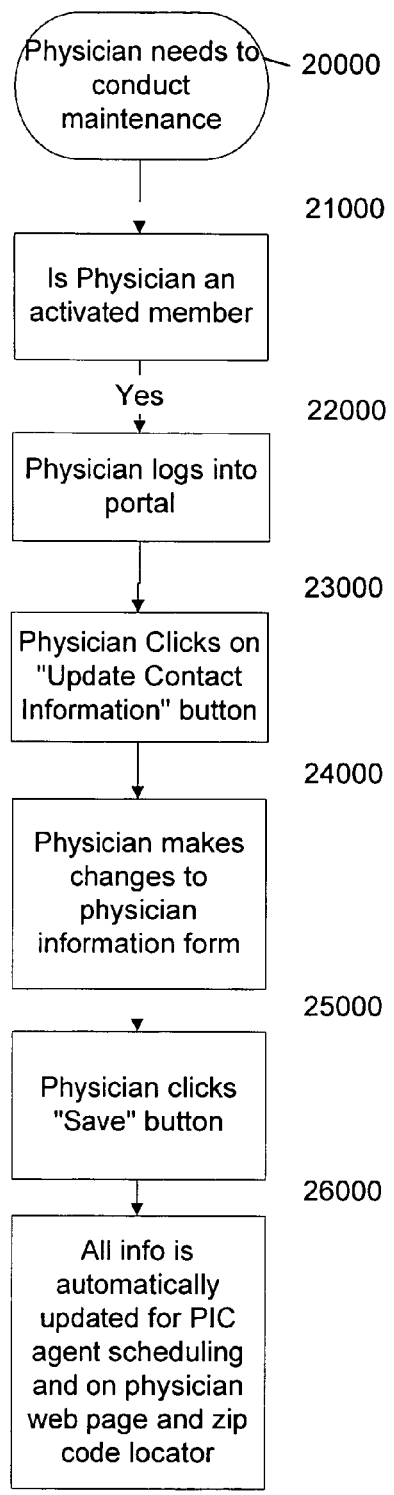

If the physician supplied website information for his/her practice (FIG. 3; step 11000), a link may be created from the zip code locator to the physician's web page (FIG. 3; step 12000) and a "welcome on board" letter is sent to the physician containing a Username and Password (FIG. 3; step 13000). The physician may then log into the database via the secure portal (FIG. 3; step 14000) and review, update, and confirm the accuracy of their contact information (FIG. 3; step 15000 through FIG. 4; step 18000) one step of which may be to reserve dedicated time slots that may allow the marketing company to book appointments on-line for potential patients (FIG. 4; step 19000). From time to time, it may become necessary for the physician to further update the information in the marketing company's database (FIG. 5; step 20000). The update protocol is outlined in steps 21000 through 26000 wherein if the physician is web-activated and authorized (FIG. 5; step 21000), the physician logs into the database via the secure portal (FIG. 5; step 22000), makes the desired changes (FIG. 5; step 24000), and when the information is saved (FIG. 5; step 25000) the updates are automatically registered in the physician's web page and entered into the zip code locator software (FIG. 5; step 26000).

With the client company and its preferred physicians under contract, the marketing company may proceed to generate a non-branded informational website relevant to the client company's products. The purpose of the non-branded website may be to attract targeted patients, family members or other interested parties of the patient with the goal of building awareness and interest in exploring a treatment option utilizing the client company's product. The first step in designing the non-branded informational website may include identifying the targeted patient population in terms of the primary medical condition for which the potential patient may be seeking treatment, and the demographics of the targeted patient population in terms of gender, age, race, geography, and the like, and identifying key motivational factors that contribute to the potential patient seeking treatment (FIG. 6A; step 30100 & 30200).

The developed website may be constructed to have the following attributes (FIG. 6A; step 30300):
1) The non-branded website preferably has no direct mention of the client company or the client company's specific products;
2) The website may have informational content focused on a specific disease state or medical condition;
3) The website may provide current, objective, medically accurate information on all available therapies for the targeted condition;
4) The website may provide a confidential toll-free phone line or e-mail address to communicate with a health care professional.

Figure 6:
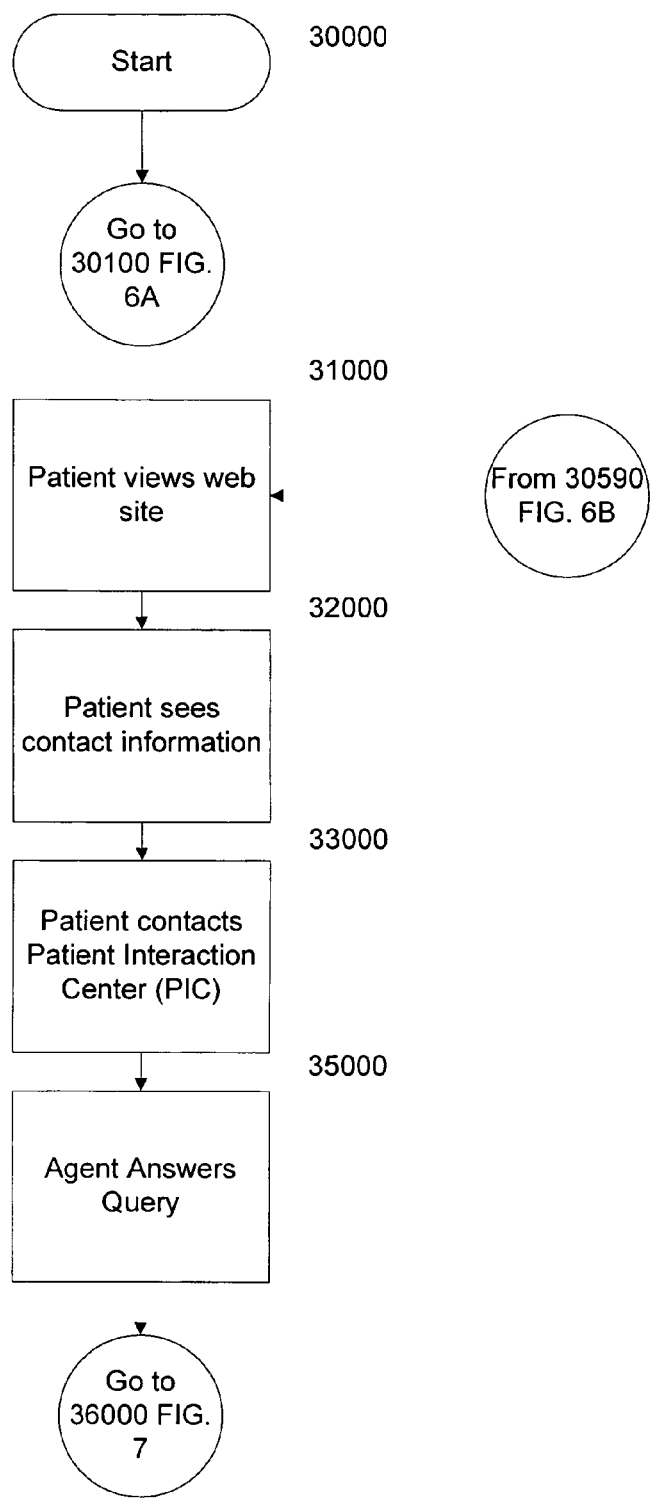
Figure 6A:
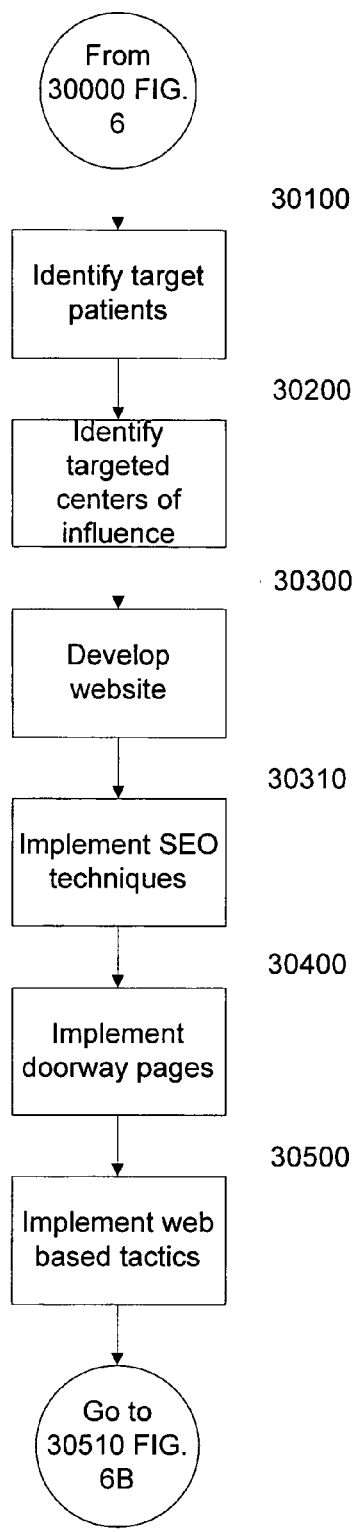

In addition to the above, the website may also be constructed to increase the probability that a potential patient browsing the internet via search engines for information relative to a medical condition that may be treated utilizing the client company's products, will be preferentially directed to the marketing company's non-branded website, hereafter referred to as search engine optimization (SEO) techniques (FIG. 6A; Step 30310). Also, doorway pages may be constructed (FIG. 6A; step 30400) which may be aimed at specific targeted audiences and may be optimized for search engine placement around a specific theme. These doorway pages may allow the marketing company to customize the home page of the non-branded website for a specific group of potential patients upon entry into the informational non-branded site. The use of doorway pages may also have the beneficial effect of increasing traffic to the non-branded website by potential patients utilizing search engines to browse the internet for relevant medical information. An example of such a doorway page may be an intentionally created website with a specific informational theme, such as "skin cancer", whereas the ultimate goal of the site may be to increase internet traffic to a linked non-branded informational website (crafted by the marketing company) on treatments for skin cancer (the client company's product).

Figure 6B:
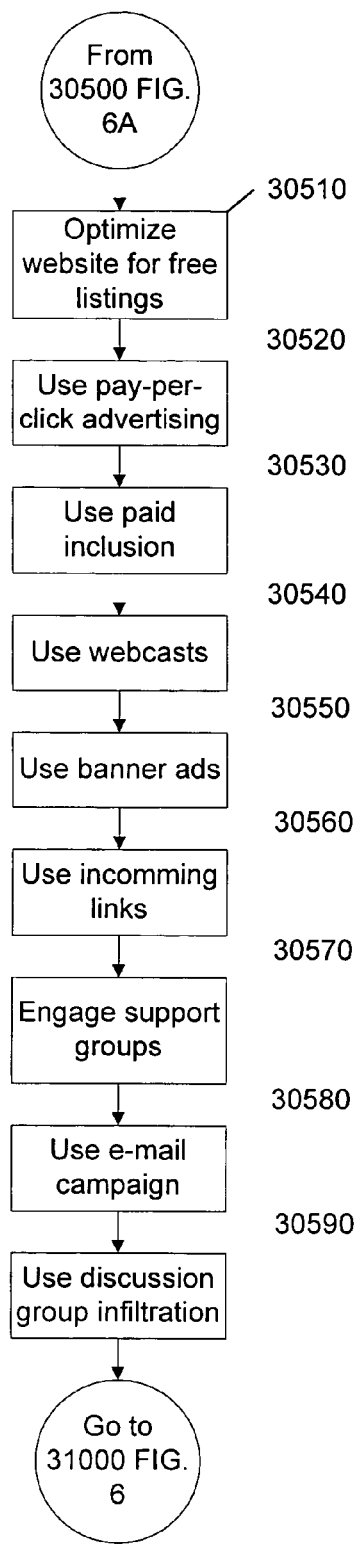

In addition to the above use of doorway pages (FIG. 6A; step 30400) there are additional web-based marketing procedures that may be employed to increase potential patient flow to the marketing company's non-branded informational website. The list of procedures may include, but is not limited to the following (FIG. 6A; step 30500):

1) Optimization of the informational website for free listings (FIG. 6B; step 30510)
2) Use of Pay-Per-Click Advertising (FIG. 6B; step 30520)
3) Use of Paid Inclusions (FIG. 6B; step 30530)
4) Webcasts (FIG. 6B; step 30540)
5) Banner Ads (FIG. 6B; step 30550)
6) Incoming Links (FIG. 6B; step 30560)
7) Support Groups (FIG. 6B; step 30570)
8) E-mail campaigns (FIG. 6B; step 30580)
9) Discussion Group Infiltration (FIG. 6B; step 30590)

Each of the above will be described in greater detail below.

Concerning optimization of the informational website for free listings (step 30510), most web-based search results are "free" to the site owners, meaning that the search engine may find the site through techniques known to those skilled in the art as "robots," "worms," or "webcrawlers", or through submissions by the site owners, which may then insert the sites into its database for retrieval by user searches. The marketing company's search engine optimization procedure for free listings may include, but is not limited to, the following four steps:

1) Coding of the pages in the non-branded informational website and content development so all important search engines and directories may properly associate them with relevant search terms
2) Submission of the website pages to the most important search engine databases and sites
3) Use of doorway pages to improve "relevance" listings and funnel traffic to the site. Doorway pages are additional Web pages that link to (or "point" to) the main marketing company's non-branded informational website and help cast a wider net
4) Regular maintenance of the search engine listings.

The use of Pay-Per-Click Advertising (FIG. 6B; step 30520) may also increase traffic to the marketing company's informational website. Pay-per-click has recently been introduced to the search engine industry, whereby advertisers bid for placement on relevant search results and pay only when a potential patient clicks on their listing. The marketing company may also utilize a paid inclusion program (FIG. 6B; step 30530) whereby advertisers (the marketing company) pay for hits to their website typically in one of two ways (or both):

1) A one-time fee for each web page submitted
2) A flat price only when a listing receives clicks Webcasts (FIG. 6B; step 30540) can be live (synchronous) or archived (asynchronous). Webcasts can be created for specific websites as a "joint venture" or as a central marketing event publicized by many websites. It may also be beneficial to have the webcast publicize the website so prospective patients can be drawn there for tracking and linking to designated physicians, or the marketing company may also purchase banner ads (FIG. 6B; step 35550) on other websites to attract patients to the non-branded "client's" informational website.

The marketing company may also utilize incoming links (FIG. 6B; step 30560) to provide a source of traffic that may greatly improve the placement of the marketing company's site in the search results of the major search engines, all of which typically rely on a "link analysis" to help them determine the relevancy of the listed site. In this scenario, a higher relevance (i.e., more links from sites with similar technical content) generally delivers a more favorable position in the search results. Given this, the marketing company may identify appropriate websites from which to obtain incoming links, solicit incoming links, and provide reciprocating links as appropriate. Support groups (FIG. 6B; step 30570) may also prove to be beneficial to the marketing company's efforts. In addition to seeking incoming links (FIG. 6B; step 30560) from the websites of support groups, the marketing company may also develop a relationship that involves the providing of additional educational materials to their members possibly via a mass E-mail campaign (FIG. 6B; step 30580) and/or participating in local meetings. Additional E-mail campaigns may be instituted by polling suitable health care sites (e.g., webmd.com) on the web and ask them to bid on submitting names of likely prospective patients gleaned from their "opt-in" mailing lists. A highly targeted mass e-mail may then be sent to this qualified list, inviting the individuals to visit the marketing company's site.

Also, the marketing company may solicit the preferred physicians to provide e-mail addresses of their likely prospective patients; in this case, the e-mail would go out under the name of the preferred physician or its clinic.

And lastly, the marketing company may utilize a procedure known as discussion group infiltration (FIG. 6B; step 30590) to increase traffic to its non-branded informational website with the ultimate goal of increasing patient flow to the preferred physicians. In one embodiment, discussion group infiltration (FIG. 6B; step 30590) may be the personal monitoring of select discussion groups and the insertion of appropriate messages. There are a number of relevant discussion groups. Some of the most popular are newsgroups. The newsgroups may be "spidered" by the major search engines for links to websites and in many cases are considered incoming links (FIG. 6B; step 30560) for the website, which may help improve site relevancy and search result position. In addition, participants in these discussion groups may be steered toward the website by judicious insertion of messages containing the URL of the website.

Figure 7:
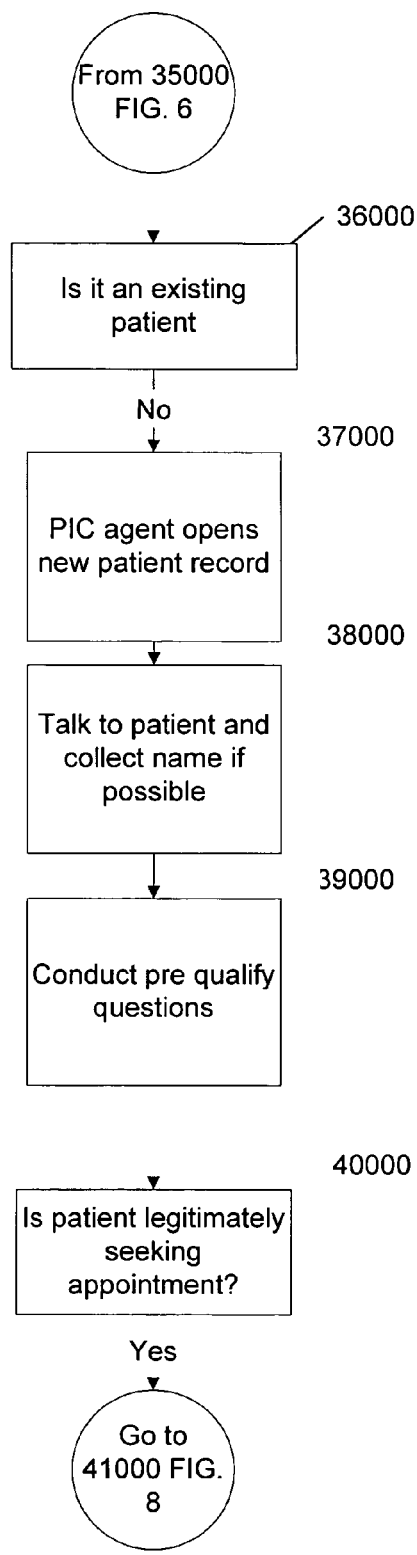

With any or all of the above techniques in place which may preferentially direct a "web-browsing" potential patient to the marketing company's website (FIG. 6B; steps 30510 through 30590), the potential patient may view the website (FIG. 6; step 31000) and may come across the contact information for the Patient Interaction Center (FIG. 6; step 32000). Wherein the potential patient may choose to contact the Patient Interaction Center (FIG. 6; step 33000) either by phone or other means for real-time access to information relevant to the patient's specific medical condition. The Patient Interaction Center Agent (PIC Agent) may take the call and answer initial questions posed by the caller (FIG. 6; step 35000). The PIC Agent may then attempt to determine if the caller is an existing patient (FIG. 7; step 36000) or a potential new patient. In the event the caller is not an existing patient, the PIC Agent may open a new patient record (FIG. 7; step 37000) and attempt to collect the potential patient's name if possible (FIG. 7; step 38000) and may begin to conduct real-time pre-qualifying questions (FIG. 7; step 39000). The pre-qualifying questions may include the following;

1) verifying that specific alternative medical options for treating the patient's medical condition have been tried and failed;
2) interactively querying the interested party as to the potential patient's medical condition with respect to the subject matter of the web site;
3) interactively querying the interested party as to the potential patient's symptoms with respect to the subject matter of the web site;
4) interactively querying the interested party as to the potential patient's current medical treatment with respect to the subject matter of the web site;
5) interactively querying the interested party as to the potential patient's use of interventional therapies, drugs or devices or adverse reactions with respect to the subject matter of the web site;
6) verifying that specific alternative medical options for treating the patient's medical condition have been evaluated and rejected;
7) verifying that the potential patient has medical insurance or alternative means to pay for medical treatments.

Figure 8:
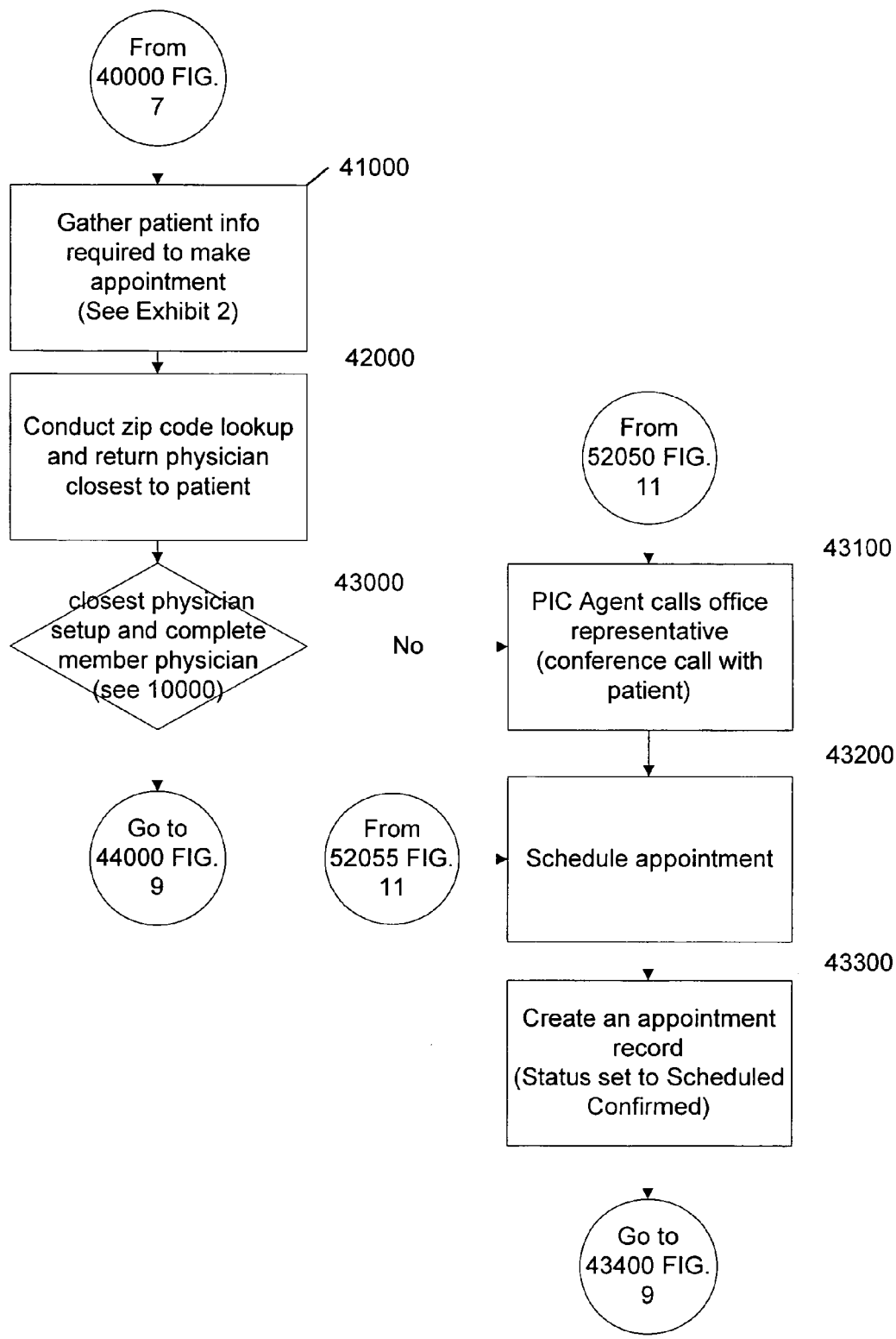
Figure 9:
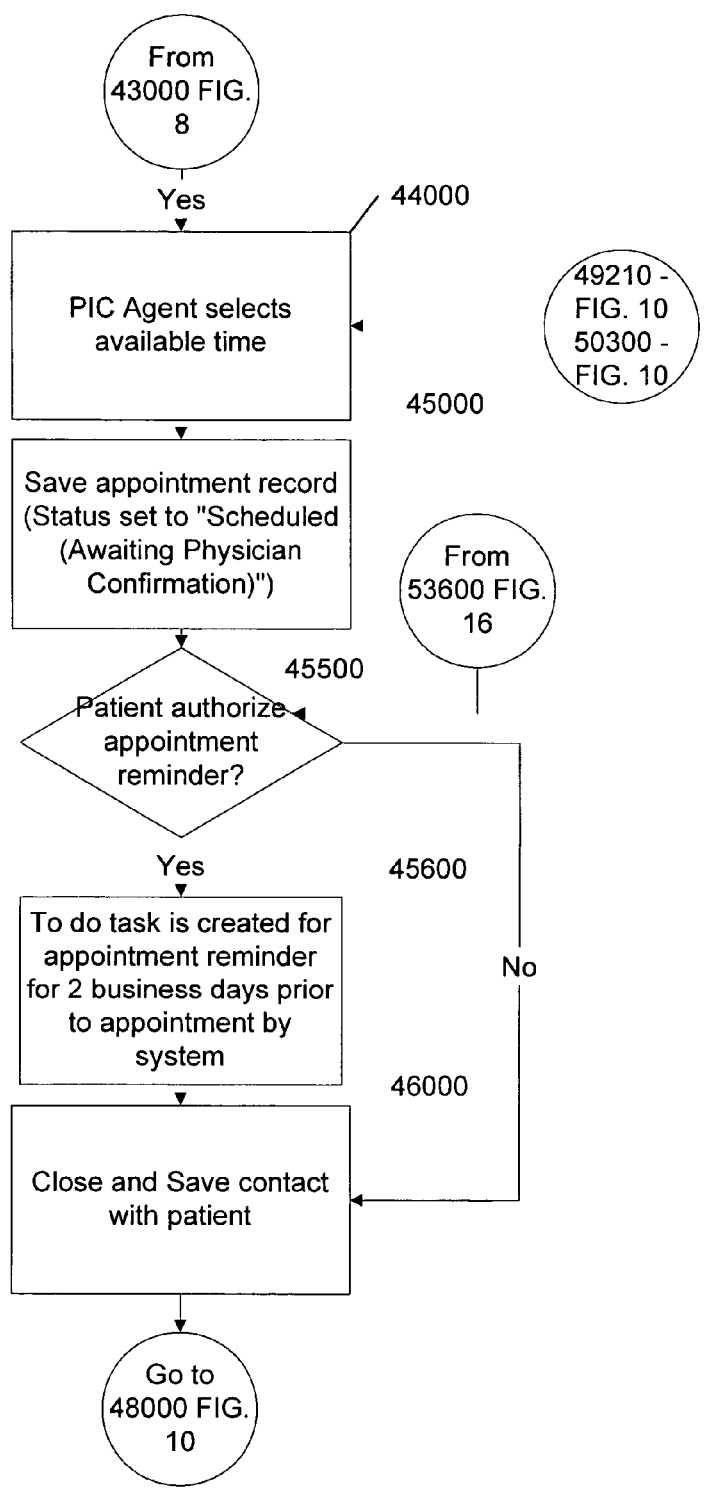

From the answers received from the pre-qualifying questions (FIG. 7; step 39000), the PIC agent may attempt to determine if the potential patient is seeking an appointment (FIG. 7; step 40000), and if so, the PIC agent may begin to gather pertinent information required to make an appointment with a preferred physician (FIG. 8; step 41000). If the potential patient consents, the PIC agent may assist in making an appointment for the patient by first locating the nearest preferred physician via the postal (zip) code locator software (FIG. 8; step 42000) and if the closest preferred physician is an established member and user set-up has been completed (FIG. 8; step 43000) the PIC Agent may select an appointment time (FIG. 9; step 44000) from the available time slots entered by the preferred physician in the company's database. Or, if the potential patient seeks immediate real-time contact with a preferred physician, the PIC Agent may initiate a 3 way teleconference connecting the potential patient with the preferred physician. Once selected, the PIC Agent may then save the appointment record in the marketing company's database and set the status of the appointment to "Awaiting Physician Confirmation" (FIG. 9; step 45000). If the patient authorizes an appointment reminder (FIG. 9; step 45500) the PIC Agent may create an entry in the "To Do" section of the company's database to contact and remind the patient within a specific time period, preferably 2 business days prior to the scheduled appointment (FIG. 9; step 45600). When completed, the PIC Agent may then save the patient record information in the marketing company's database (FIG. 9; step 46000).

Figure 10:
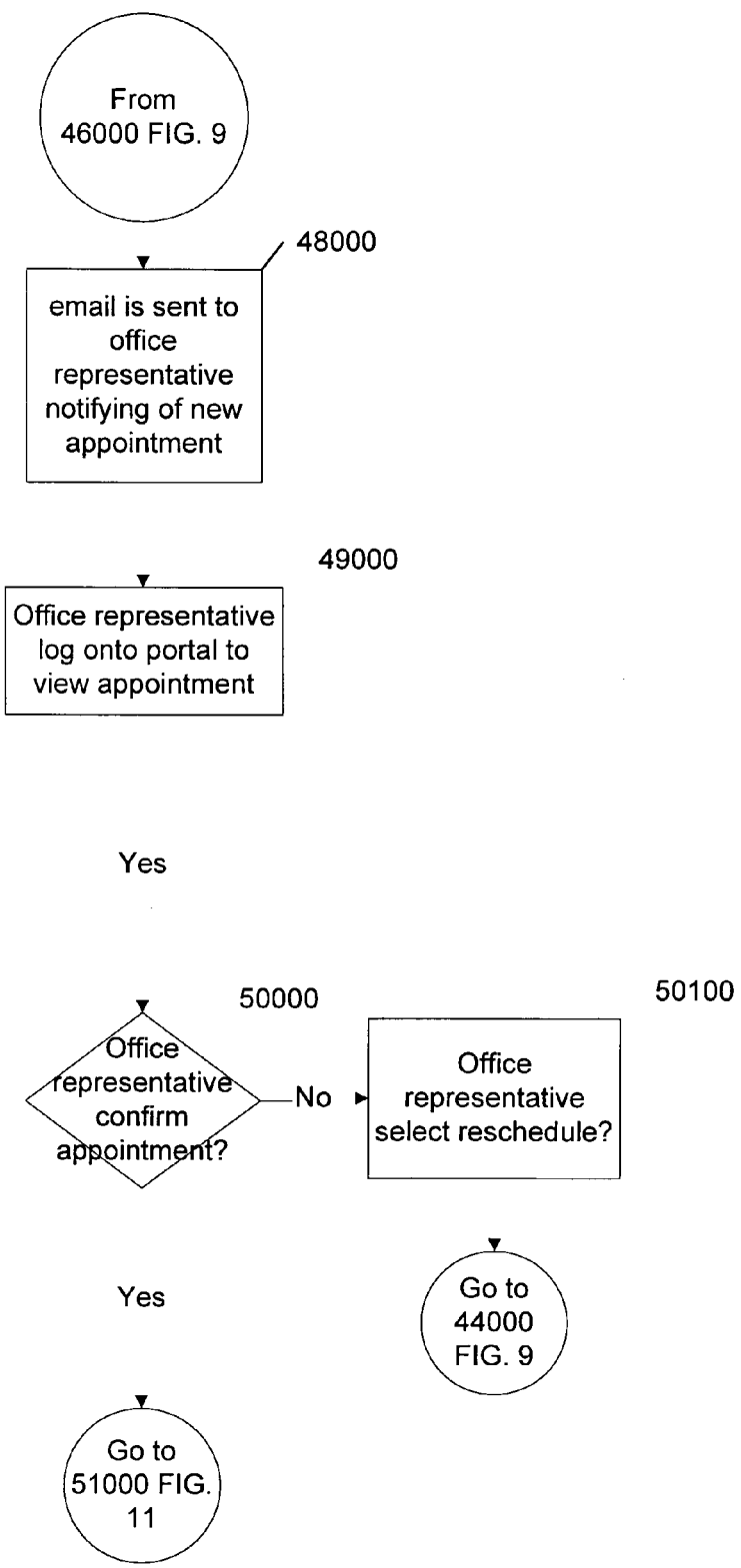
Figure 11:
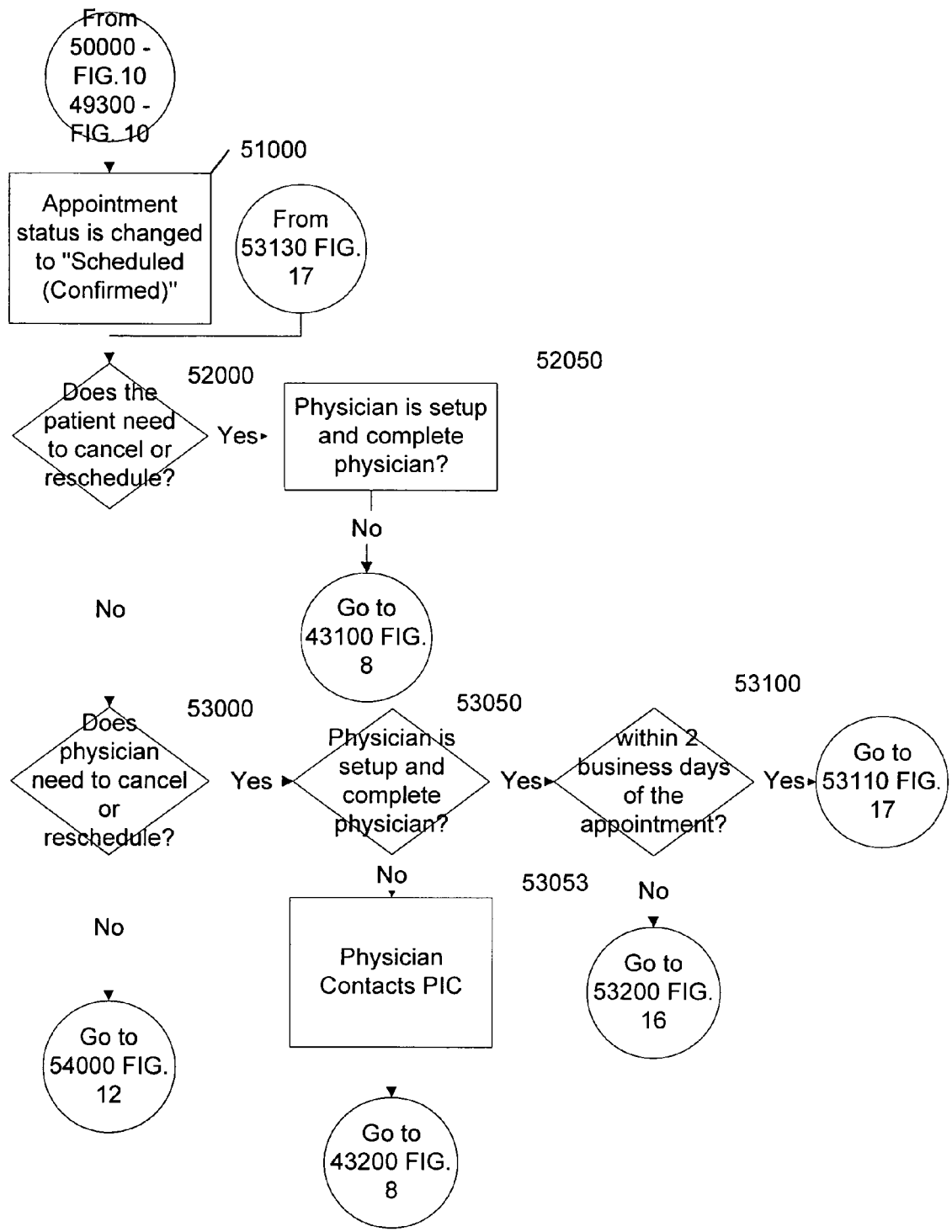

The PIC software may then send an E-mail to the preferred physician notifying him/her that a pending appointment has been entered into the marketing company's database (FIG. 10; step 48000). The E-mail may contain no direct mention of the patient's name or any other confidential data associated with the patient. Once received, the physician or his/her authorized office representative may log into the marketing company's database via the secure portal to record the patient's data and scheduled appointment time (step 49000) and may either confirm (FIG. 10; step 50000) or choose to re-schedule (FIG. 10; step 50100) the appointment. Once confirmed by the physician or his/her office representative, the status of the patient's scheduled appointment is set to "Confirmed" in the marketing company's database (FIG. 11; step 51000). In the interim between confirming the appointment (FIG. 11; step 51000) and the scheduled appointment date, either the patient or physician may need to cancel or re-schedule the appointment. In the case where the patient may need to cancel or re-schedule the appointment (FIG. 11; step 52000), the patient may contact the PIC Agent to assist in either case. If the preferred physician is enrolled in the marketing company's program, i.e., a set-up and complete preferred physician (FIG. 11; step 52050), the PIC Agent may contact the physician or office representative by phone, or other means, to re-schedule the appointment. The PIC Agent may choose to initiate a 3 way conference call with the physician's office and patient (FIG. 8; step 43100) to facilitate re-scheduling the appointment (FIG. 8; step 43200) and once re-scheduled, the PIC Agent may create an appointment record in the marketing company's database and set the status in the database to "Confirmed" (FIG. 8; step 43300).

Figure 12:
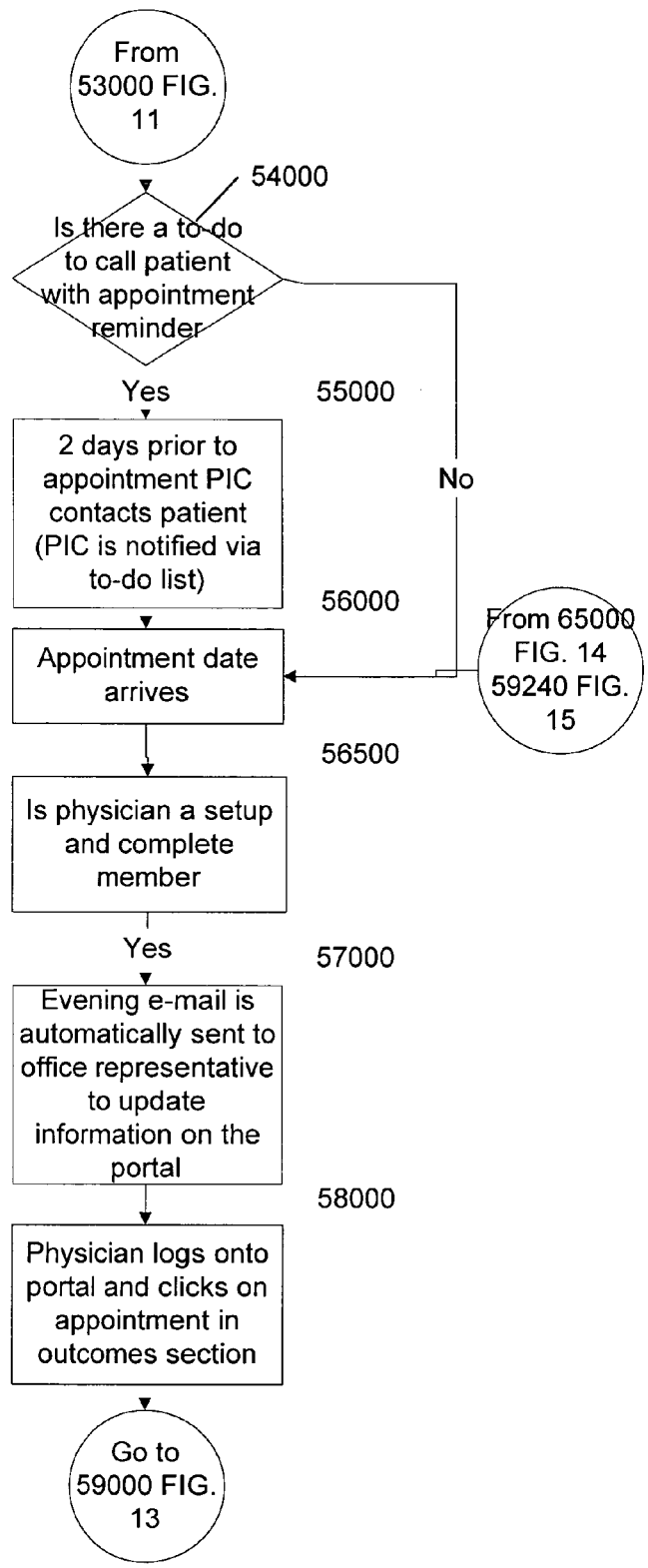
Figure 13:
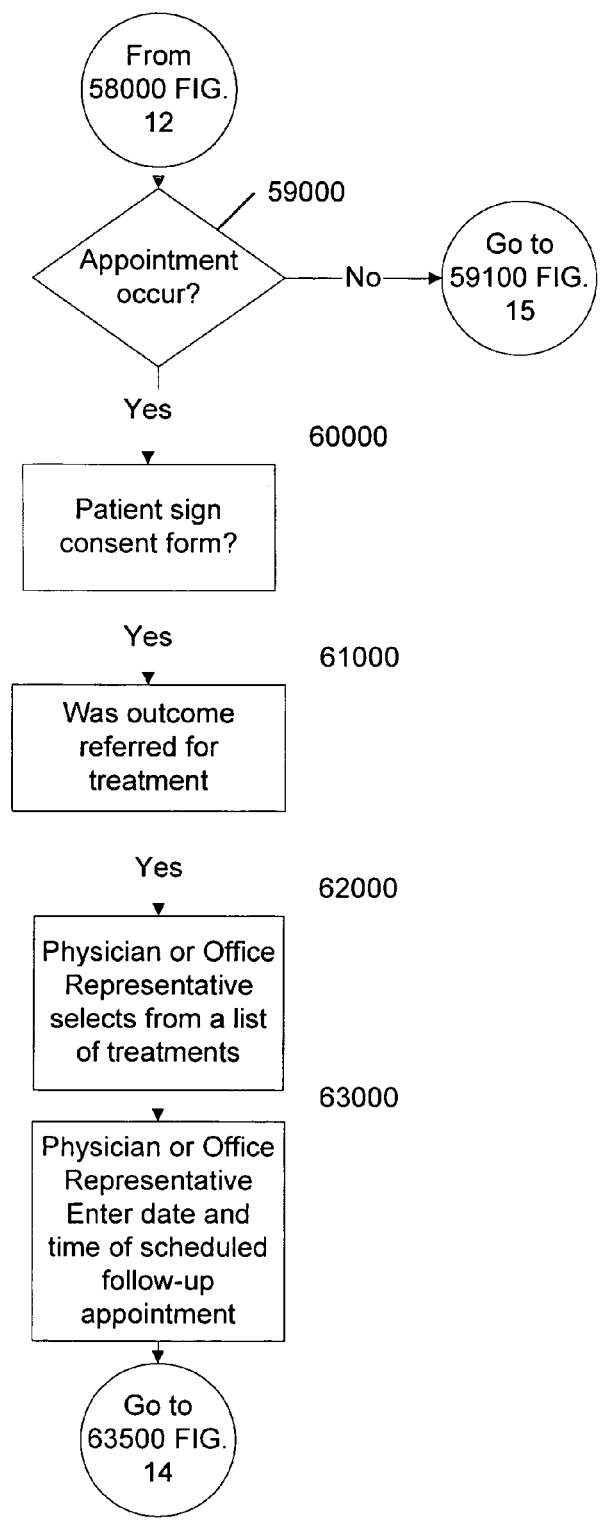
Figure 14:
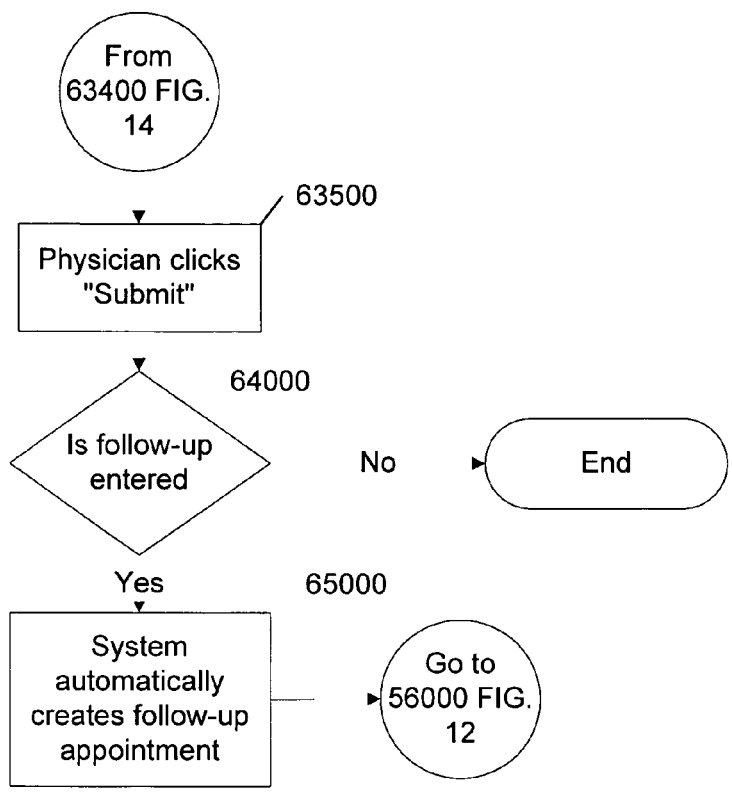

Similarly, in the interim between confirming the appointment (FIG. 11; step 51000) and the scheduled appointment date, the preferred physician may need to cancel or re-schedule the appointment (FIG. 11; step 53000). In the case where the preferred physician is enrolled in the marketing company's program, i.e., a set-up and complete preferred physician (FIG. 11; step 53050), the physician may either contact the PIC Agent (FIG. 11; step 53053) to assist in the process, or if time is of the essence, e.g., the appointment may be within a specific time period, preferably 2 business days (FIG. 11; step 53100), the physician may contact the patient directly to cancel or re-schedule (FIG. 18; steps 53110 through 53130) the appointment. Or, however, if time is not of the essence, e.g., the appointment may be greater than a specific time period, preferably greater than 2 business days (FIG. 11; step 53100), the physician may utilize the secure portal to cancel or re-schedule (FIG. 16; steps 53200 through 53600) the appointment. If neither patient nor physician initiates a cancellation or re-schedule request in the interim between appointment confirmation (FIG. 8; step 43300) and within a specific time period, preferably 2 business days prior to the appointment, and if the patient authorized an appointment reminder (FIG. 12; step 54000), the PIC Agent may be notified by an electronic reminder, or other means, to contact the patient within a specific time period, preferably 2 business days prior to the appointment (FIG. 12; step 55000). If the physician is an established member and user set-up has been completed (FIG. 12; step 56500), on the evening of the appointment date (FIG. 12; step 56000) an E-mail may be sent to the physician's office representative as a reminder to update the patient's file after the office visit utilizing the secure portal entry to the marketing company's database (FIG. 12; step 57000). The physician may then log into the database via the secure portal (FIG. 12; step 58000) and verify whether or not the appointment actually occurred (FIG. 13; step 59000), and may confirm if the patient signed the appropriate consent form (FIG. 13; step 60000). If the patient signed the appropriate consent form, the physician may make an entry into the marketing company's database via the portal as to whether the patient was referred to follow-on treatment (FIG. 13; step 61000). The physician or office representative may then update the patient's database file with the recommended follow-on treatment (FIG. 13; step 62000) and log the scheduled appointment for such treatment (FIG. 13; step 63000 through FIG. 14; 64000), wherein the database software may automatically create the follow-up appointment (FIG. 14; step 65000).

Figure 15:
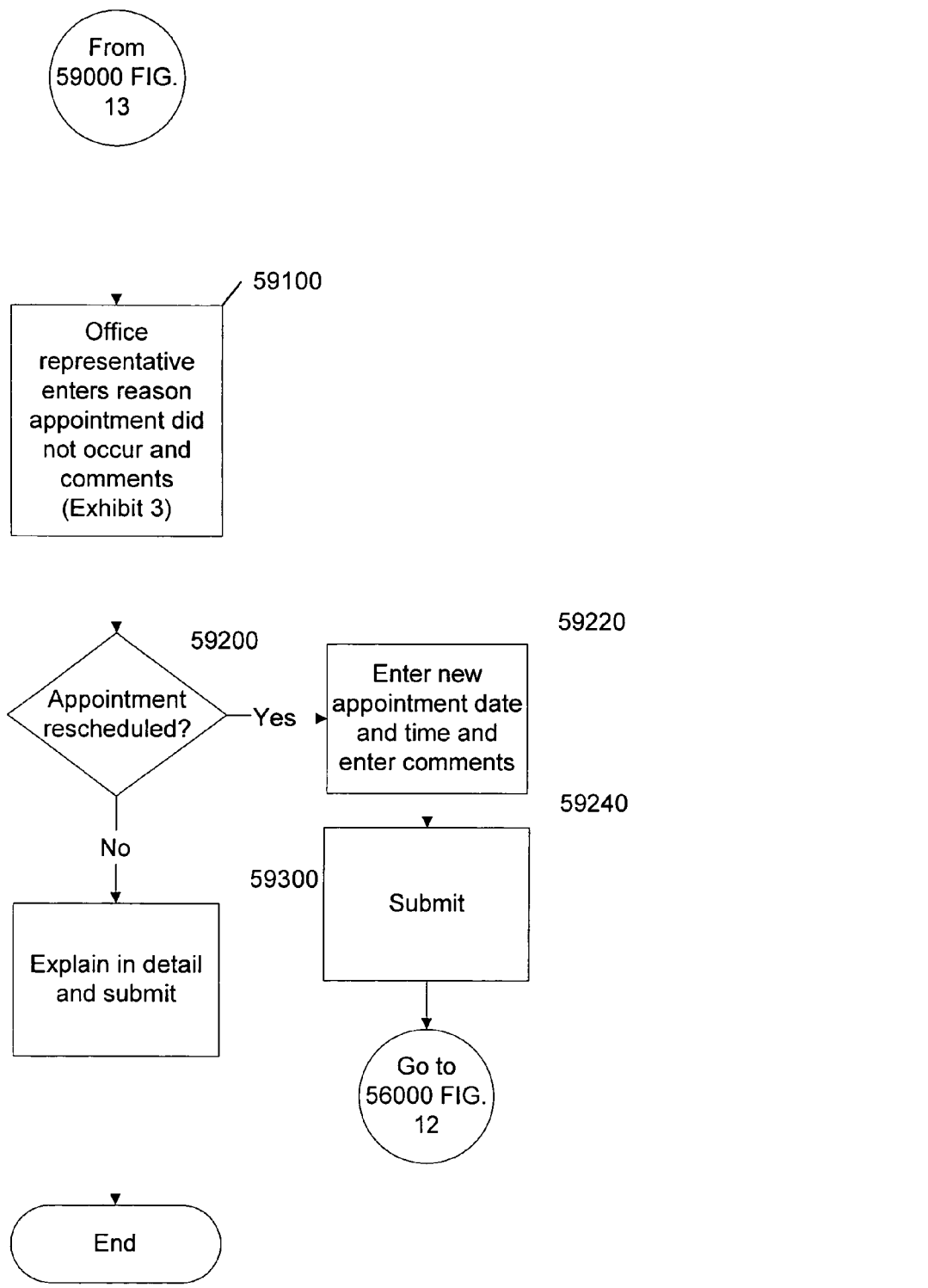
Figure 16:
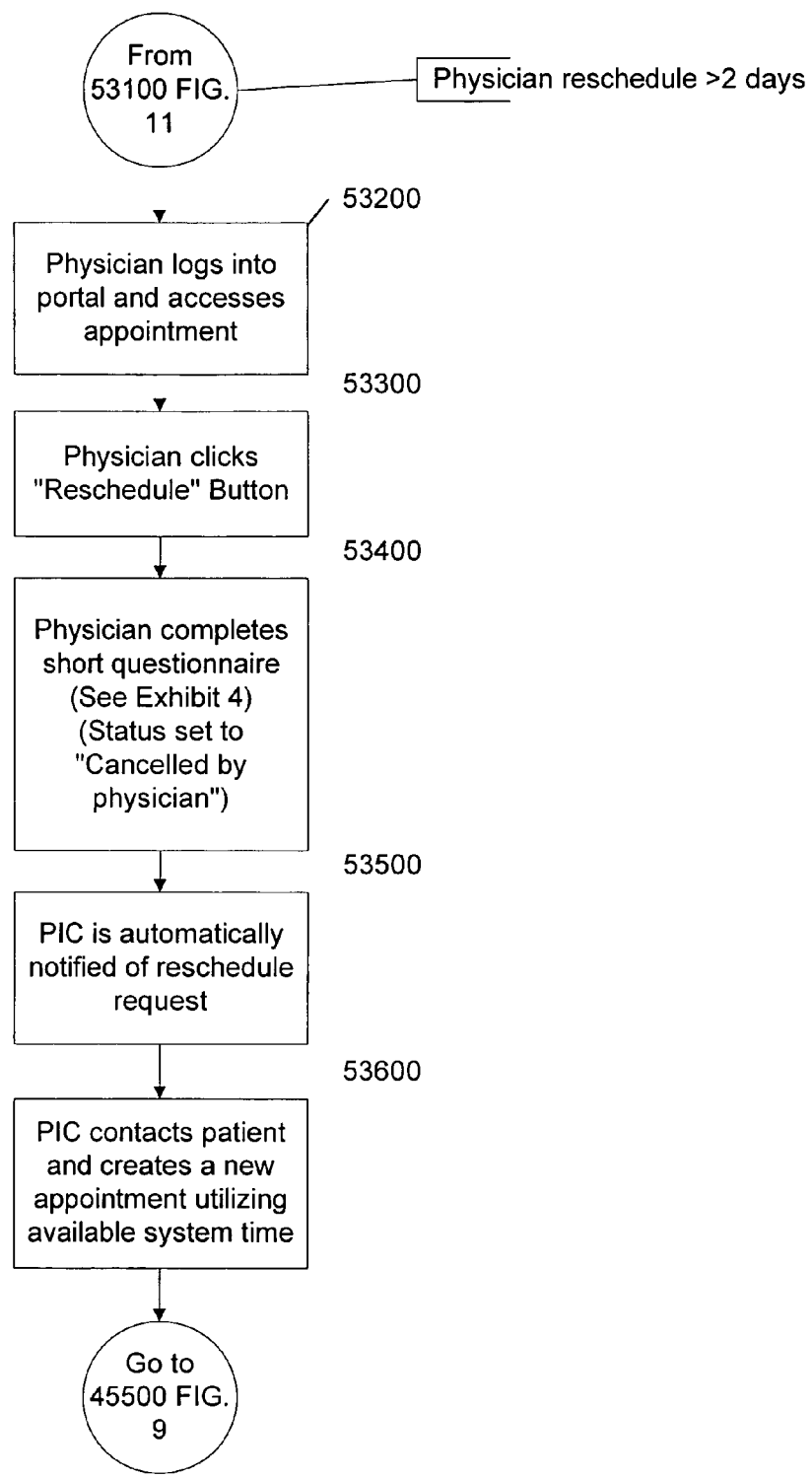
Figure 17:
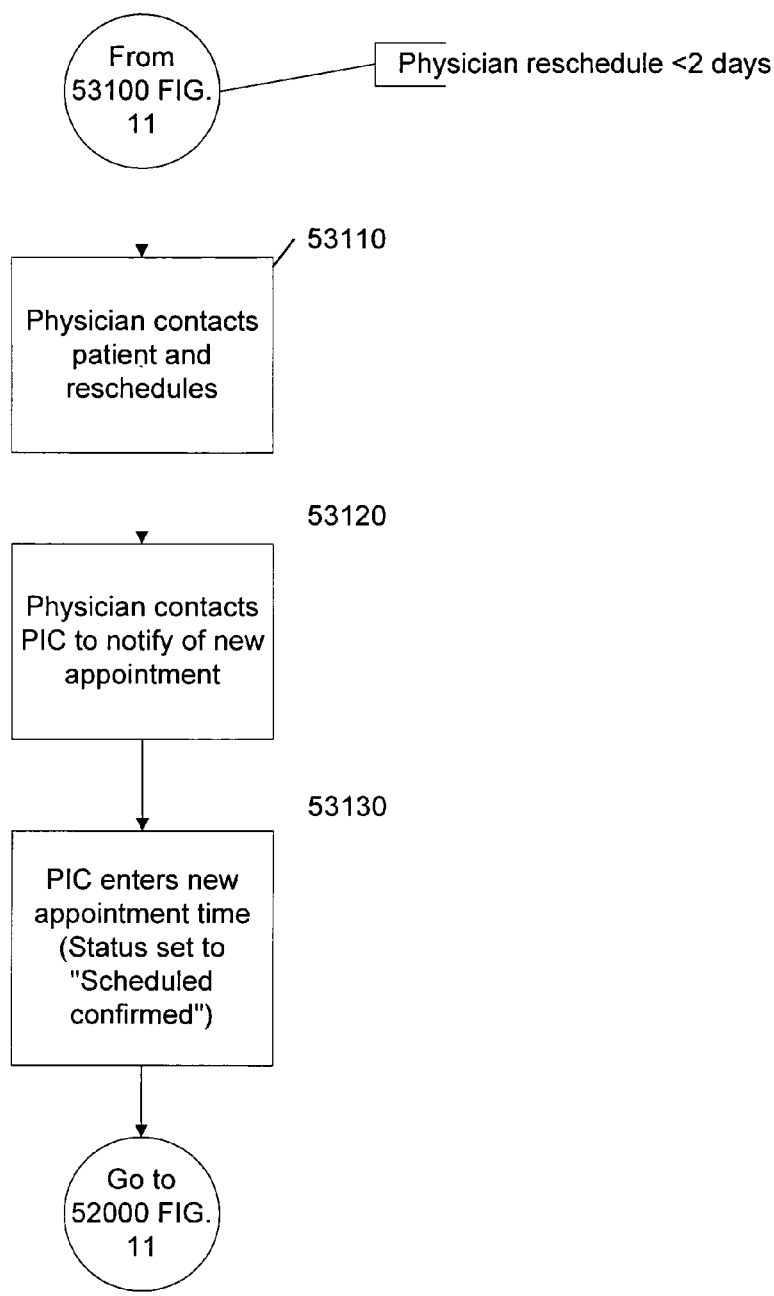

In the event the patient did not cancel or re-schedule the original appointment, but nonetheless did not make the appointment, e.g. a "no-show", the office representative may attempt to discern the reason for missing the appointment and may log the results in the marketing company's database (FIG. 15; step 59100). If the patient chooses, the office representative may reschedule the appointment (FIG. 15; steps 59200 through 59240) or, if the patient chooses not to re-schedule the appointment, the office representative will attempt to discern the reason and input the information in the marketing company's database via the secure portal (FIG. 15; step 59300).

Figure 18:
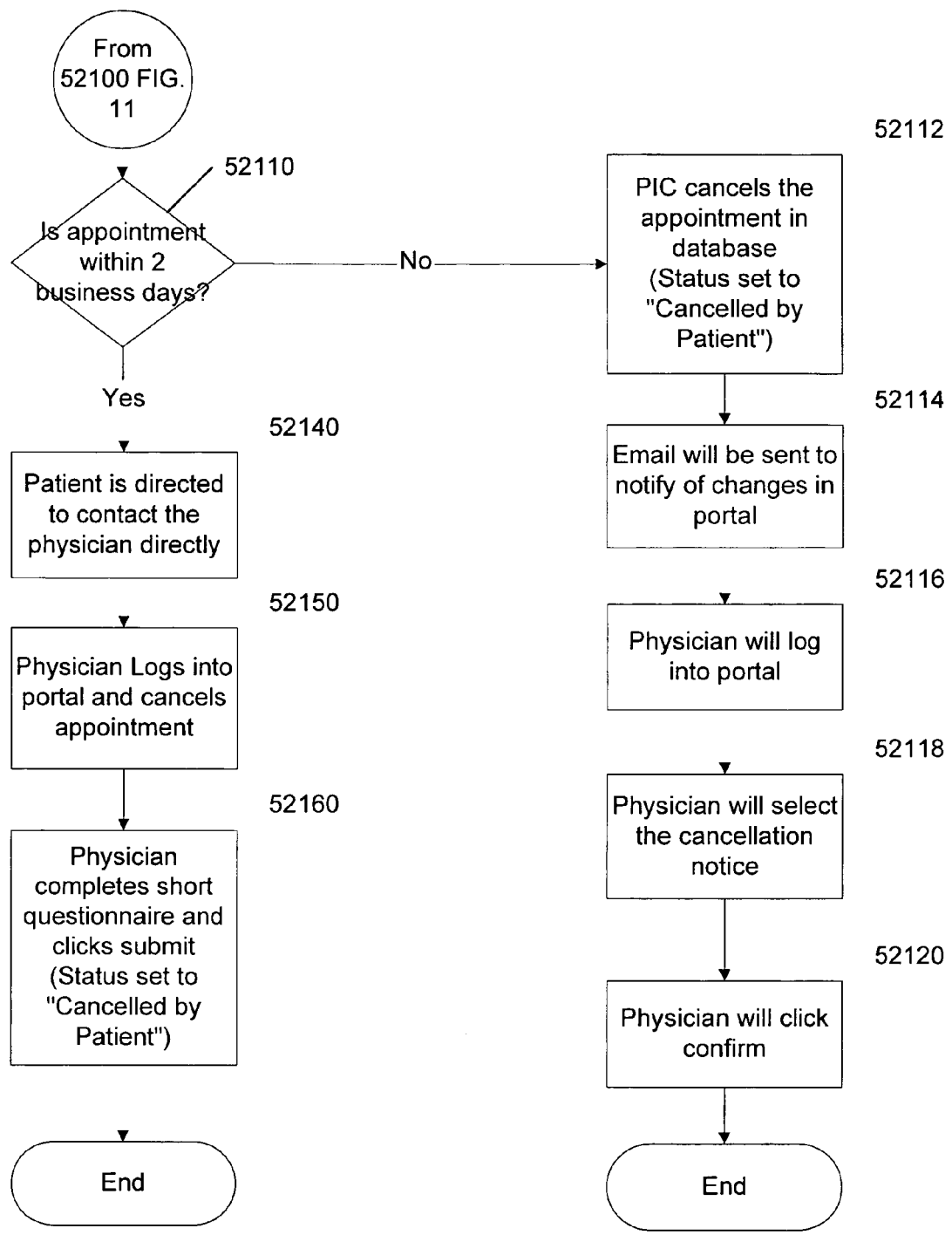

If, however, the patient chooses to outright cancel the appointment (i.e., no re-scheduling), and if the appointment has drawn near, say within a specific time period, preferably 2 business days (FIG. 18; step 52110), the patient may be advised to cancel the appointment directly with the physician's office (FIG. 18; step 52140). Once contacted by the patient, the physician may log into the marketing company's database via the secure portal (FIG. 18; step 52150) and complete the cancellation questionnaire and the PIC software automatically sets the patient's status to "Cancelled by Patient" (FIG. 18; step 52160). Alternatively, if the patient chooses to cancel well in advance of the appointment date, say for example greater than 2 business days prior to the appointment, the patient may contact the PIC Agent who will cancel the appointment in the marketing company's database (FIG. 18; step 52112) and forward an e-mail to the physician signifying changes in the database that may be reviewed via the secure portal (FIG. 18; step 52114). The physician may then log into the portal and confirm the patient's cancellation (FIG. 18; steps 52116 through 52120).

Another embodiment of the present invention is directed to the case where the marketing company generates and maintains a non-branded website which has multiple clients, each with their own list of preferred health care professionals (vendors). The multiple clients may span a broad array of medical products or therapies including but not limited to; cancer diagnostics and therapeutics, surgical instruments, diabetes products, cardiovascular implants, sexual disfunction products, interventional drugs, and the like. In this case, the non-branded website may be designed to attract interested parties and/or potential patients seeking general information about a medical condition or therapy. Given this, the PIC Agent (booking agent) may first qualify the interested party and/or potential patient as to which client company's particular product or therapy best suits the needs of the potential patient. Once the PIC Agent has identified the particular client company which best provides products or therapies given the potential patient's medical condition, the PIC Agent may begin the procedure of connecting the potential patient to their preferred health care professionals, assisting in booking an appointment with one of their preferred health care professional, and tracking outcomes in the manner described earlier.

As noted above, the present invention is applicable to marketing techniques and is believed to be particularly useful for direct-to-patient marketing for medical products and procedures. The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A method for marketing of a client's medical product or therapy to a patient via a marketer's web site, comprising:
   a. finding potential patients who are suitable candidates for a specific medical condition including the steps of;
      1) posting a non-branded, informational website with information relevant to the specific medical condition;
      2) providing interactive technical assistance reachable via the site to assist potential patients with questions relating to said specific medical condition;
   b. qualifying interested parties utilizing predetermined criteria comprising;
      verifying whether specific alternative medical options for treating the patient's medical condition have been considered, including the steps of
         1) interactively querying the interested party as to the potential patient's medical condition with respect to the subject matter of the web site,
         2) verifying whether specific alternative medical options for treating the patient's medical conditions, not supported by the client's product or therapy, have been considered and rejected;
      connecting the qualified interested party to at least one preferred health care professional capable of offering the client's specific product comprising;
         1) contracting, in advance, with preferred health care professionals which can provide medical services utilizing client's product or therapy,
         2) querying a database of said preferred health care professionals providing the patient with a preferred health care professional most appropriate to the patient;
      in advance of booking appointments, contracting with preferred health care professionals to obtain pre-approved appointment slots which may be scheduled by the marketer; and storing said data in marketer's data base;
      querying the patient to schedule an appointment for the patient with a preferred health care professional drawing from the data base of pre-approved appointment slots.

2. The method of claim 1 wherein said health care professional providing step is based on the professional most geographically convenient to the patient.

3. The method of claim 1 wherein said vendor providing step includes providing professionals names based on objective criteria associated with selection of professionals from the database.

4. The method of claim 1 wherein said qualifying step includes:
   interactively querying the interested party as to the potential patient's current medical treatment with respect to the subject matter of the web site.

5. A method for marketing of a client's medical product or therapy to a patient via a marketer's web site, comprising:
   a. finding potential patients who are suitable candidates for a specific medical condition including the steps of;
      1) posting a non-branded, informational website with information relevant to the specific medical condition;
      2) providing interactive technical assistance reachable via the site to assist interested parties with questions relating generally to said specific medical condition;
   b. qualifying interested parties utilizing predetermined criteria comprising;

verifying that specific alternative medical options for treating the patient's medical condition have been considered, including the steps of
1) interactively querying the interested part as to the potential patient's medical treatment with respect to the subject matter of the web site;
verifying that the potential patient has means to pay for medical treatments;
c. connecting the qualified interested party to at least one preferred health care professional capable of offering the client's specific product comprising;
1) contracting in advance with preferred health care professionals which can provide medical services utilizing client's product or therapy,
2) querying a database of said preferred health care professionals
3) providing the patient with a preferred health care professional most appropriate to patient;
in advance of booking appointments, contracting with preferred health care professionals to obtain pre-approved appointment slots which may be scheduled by the marketer; and storing said data in marketer's data base;
querying the patient to schedule an appointment for the patient with a preferred health care professional drawing from the data base of pre-approved appointment slots;
issuing a confirmatory communication from marketer's database to preferred health care professional, referring to the patient by indirect data so as not to transmit name identifiable patient data over a communications channel, confirming that the time slot provided by contract is now engaged and blocking that slot from further use;
in response to said confirmatory communication, allowing the health care professional to query the marketer's secure portal and obtain patient data corresponding to that patient for said time slot;
monitoring the secure portal to confirm that the health care professional has accessed and retrieved the patient data.

6. The method of claim 5 wherein said providing step is based on the health care professional most geographically convenient to the patient.

7. The method of claim 5 wherein said providing step includes providing health care professional names based on objective criteria associated with selection of professionals from the database.

8. The method of claim 5 wherein the finding step includes:
in response to the contact by the interested party, interactively collecting information from said interested party concerning as to how they found the web site; and
periodically optimizing the website by modifying its contents in response to the survey information to increase the probability that interested parties searching the internet for information about the specific medical condition will be directed to the site.

9. The method of claim 5 wherein the qualifying step includes:
interactively querying the interested party as to the potential patient's medical condition with respect to the subject matter of the web site;
1) interactively querying the interested part as to the potential patient's current medical treatment with respect to the subject matter of the web site; and
2) verifying that specific alternative medical options for treating the patient's medical conditions, not supported by the client's product or therapy, have been considered.

10. The method of claim 5 wherein the connecting step includes:
upon obtaining patient consent, recording patient information in marketer's database and making patient information available only to preferred health care professionals by way of a secure portal.

11. A method for marketing of a client's medical product or therapy to a patient via a marketer's web site, comprising:
a. finding potential patients who are suitable candidates for a specific medical condition including the steps of;
1) Posting a non-branded, informational website with information relevant to the specific medical condition;
2) providing online technical assistance reachable via the site to assist interested parties with questions relating generally to said specific medical condition;
3) inviting interested parties to contact health care professionals knowledgeable of said medical condition via the web site
b. qualifying interested parties utilizing a predetermined criterion comprising;
verifying that specific alternative medical options for treating the patient's medical condition have been tried and failed, including the steps of
1) interactively querying the interested party as to the potential patient's medical condition with respect to the subject matter of the web site;
2) interactively querying the interested part as to the potential patient's symptoms with respect to the subject matter of the web site;
3) interactively querying the interested part as to the potential patient's current medical treatment with respect to the subject matter of the web site;
4) interactively querying the interested part as to the potential patient's use of interventional therapies, drugs or devices or adverse reactions with respect to the subject matter of the web site;
verifying that specific alternative medical options for treating the patient's medical condition have been evaluated and rejected;
verifying that the potential patient has means to pay for medical treatments;
c. connecting qualified interested parties to a preferred health care professional capable of offering the client's specific product comprising;
1) querying a database of preferred health care professionals
2) providing the patient with a preferred health care professional appropriate to patient;
3) initiating an on-line connection with said appropriate preferred health care professional;
4) collecting patient information and storing it in the marketer's on-line secure database for communication between the web site and the preferred health care professional;
recording patient information in marketer's database and making patient information available only to preferred health care professionals by way of a secure portal;
in advance of booking appointments, contracting with preferred health care professionals to obtain pre-approved appointment slots which may be scheduled by the marketer; and storing said data in marketer's data base;
scheduling an appointment for the patient with a preferred health care professional drawing from the data base of pre-approved appointment slots;
automatically issuing a confirmatory communication from marketer's database to preferred health care professional, referring to the patient by indirect data so as not to transmit name identifiable patient data over a communications channel, confirming that the time slot provided by contract is now engaged and blocking that slot from further use;

in response to said confirmatory communication, the health care professional queries the marketer's data base by way of the secure portal and obtains patient and payment data corresponding to that patient for said time slot;

monitoring the secure portal to confirm that the health care professional has accessed and retrieved the patient data;

d. tracking patient progress from scheduled appointment to outcome comprising;

receiving consent from potential patient to remind patient of upcoming appointments with the preferred health care professional;

issuing a reminder to the patient of scheduled appointment within a specific time interval before upcoming appointment with the preferred health care professional.

12. The method of claim 11 wherein the connecting step includes:

interactively collecting survey information from interested parties viewing the website concerning as to how they found the web site; and periodically optimizing the website by modifying its contents in response to the survey information to increase the probability that potential patients searching the internet for information about the specific medical condition will be directed to the site.

13. The method of claim 11 wherein the connecting step includes:

receiving authorization from the potential patient to contact their medical insurance carrier to verify reimbursement coverage for the specific medical product or therapy.

14. The method of claim 11 wherein the connecting step includes:

querying a data base of information specific to the potential patient's geographical area to determine, with some degree of probability, that the potential patient's insurance policy will cover the cost of the client's medical product or therapy.

15. The method of claim 11 wherein the connecting step includes:

maintaining a database of financial institutions that provide financial assistance to potential patient's without reimbursement coverage for the client company's specific product or therapy.

16. The method of claim 11 wherein the connecting step includes:

referring potential patients to possible financing sites in the event that potential patient's insurance carrier does not reimburse client company's specific product or therapy.

17. The method of claim 11 wherein the connecting step includes:

after the scheduled appointment time slot has passed, confirming that the patient attended scheduled appointment by issuing a communication to the health care professional requesting information to track the progress of treatment; and repeating the tracking until the health care professional confirms conclusion of treatment so that the marketer has a complete record of treatment of the patient's condition and can assemble a data base of like experiences from other patients via the web site.

18. A method for marketing of a client's medical product or therapy to a patient via a marketers web site, comprising:

a. finding potential patients who are suitable candidates for a specific medical condition including the steps of;

1. posting a non-branded, informational website with information relevant to the specific medical condition;

2. providing interactive technical assistance reachable via the site to assist interested parties with questions relating generally to said specific medical condition;

b. qualifying interested parties utilizing a predetermined criterion comprising;

verifying that specific alternative medical options for treating the patient's medical condition have been considered, including the step of c. connecting the qualified interested party to at least one preferred health care professional capable of offering the client's specific product comprising;

1. contracting in advance with preferred health care professionals which can provide medical services utilizing client's product or therapy, 2. querying a database of said preferred health care professionals 3. providing the patient with a preferred health care professional most appropriate to patient;

4. upon obtaining patient consent, recording patient information in marketer's database and making patient information available only to preferred health care professionals by way of a secure portal;

in advance of booking appointments, contracting with preferred health care professionals to obtain pre-approved appointment slots which may be scheduled by the marketer; and storing said data in marketer's data base;

querying the patient to schedule an appointment for the patient with a preferred health care professional drawing from the data base of pre-approved appointment slots;

issuing a confirmatory communication from marketer's database to preferred health care professional, referring to the patient by indirect data so as not to transmit name identifiable patient data over a communications channel, confirming that the time slot provided by contract is now engaged and blocking that slot from further use;

in response to said confirmatory communication, the health care professional queries the marketer's secure portal and obtains patient data corresponding to that patient for said time slot;

monitoring the secure portal to confirm that the health care professional has accessed and retrieved the patient data.

19. The method of claim 18 wherein said providing step is based on the health care professional most geographically convenient to the patient.

20. The method of claim 18 wherein said providing step includes providing health care professional names based on objective criteria associated with selection of professionals from the database.

21. A method of identifying qualified patients appropriate to a plurality of clients of medical products or therapies, for redirection of patients, via a marketer's web site, to prequalified vendors of clients' products or therapies and confidentially booking appointments, in real time, comprising:

a. finding potential patients and interested parties representing patients, who are suitable candidates for medical treatment of a medical condition including the steps of;

1) posting a non-branded, informational website with information relevant to the medical conditions of clients' products and therapies and inviting interested parties and patients to interactively contact the site;

2) providing online trained assistance reachable via the site, in real time, to assist interested parties and patients with questions relating generally to their medical condition;

b. qualifying interested parties and patients by utilizing a predetermined criterion comprising the steps of:

3) interactively querying interested parties and patients as to the patient's medical condition with respect to the subject matter of the web site;

4) interactively querying interested parties and patients as to the patient's current medical treatment with respect to the subject matter of the web site;

c. making a preliminary determination as to whether any of the site's prequalified vendors may be appropriate to provide services or treatment to the potential patient;

d. connecting qualified interested parties and patients to a vendor capable of offering the client's specific product comprising;

1) querying a database for vendors who are appropriate to the patient;

2) providing interested parties and patients with the name of at least one vendor;

3) interactively querying interested parties and patients as to whether they would like the set up an appointment between the patient and one of the vendors, 4) in advance of booking appointments, contracting with vendors to obtain pre-approved appointment slots which may be scheduled by the marketer; and storing said data in marketer's data base;

5) with consent of the patient, obtaining confidential patient information and storing it in marketer's database 6) scheduling an appointment for the patient with said vendor by drawing from the data base of pre-approved appointment slots;

7) issuing a confirmatory communication from marketer's database to vendor, referring to the patient by indirect data so as not to transmit patient confidential information data over a communications channel, confirming that the time slot provided by contract is now engaged and blocking that slot from further use;

8) in response to said confirmatory communication, based on the data obtained there-from, allowing the vendor to query the marketer's data base by way of a secure portal and obtain confidential patient data corresponding to that patient for said time slot;

monitoring the secure portal to confirm that the vendor has accessed and retrieved the patient data.

22. The method of claim 21 further including the step of with the consent of the patient, periodically reporting to client progress and outcome data from the vendor with respect to each patient receiving client's product or treatment.

23. The method of claim 21 wherein said clients are competitors and where said step of providing vendors is without preference to the product or therapy of any particular client.

24. The method of claim 21 wherein said vendor providing step is based on the vendor most geographically convenient to the patient.

25. The method of claim 21 wherein said vendor providing step includes providing vendor names based on objective criteria associated with selection of vendors from the vendor database.

* * * * *

UNITED STATES PATENT AND TRADEMARK OFFICE
CERTIFICATE OF CORRECTION

| | | |
|---|---|---|
| PATENT NO. | : 7,499,866 B2 | Page 1 of 3 |
| APPLICATION NO. | : 10/440594 | |
| DATED | : March 3, 2009 | |
| INVENTOR(S) | : Mark Summers et al. | |

It is certified that error appears in the above-identified patent and that said Letters Patent is hereby corrected as shown below:

Please add drawings labeled as Exhibits 1-4 immediately following the last drawing labeled as FIG.18.

Exhibit 1
Physician: First Name Middle Initial Last Name
Practice Name:
Practice Hours:
Practice Street Address: City: State: Zip Code:
Main Phone Number:
Alternate Phone Number:
Fax Number:
Top 3-5 affiliate patient insurance networks:
1.
2.
3.
4.
5.
Top 3-5 excluded patient insurance networks:
1.
2.
3.
4.
5.

Scheduling Desk Contact Name:
Scheduling Desk Contact Direct phone number / extension:
Scheduling Desk Contact Email address:

Patient Follow-up Contact Name:
Patient Follow-up Contact Direct phone number / extension:
Patient Follow-up Contact Email address:

Reserved appointment
Monday Time One
Monday Time Two
Tuesday Time One
Tuesday Time Two
Wednesday Time One
Wednesday Time Two
Thursday Time One
Thursday Time Two

UNITED STATES PATENT AND TRADEMARK OFFICE
CERTIFICATE OF CORRECTION

PATENT NO. : 7,499,866 B2
APPLICATION NO. : 10/440594
DATED : March 3, 2009
INVENTOR(S) : Mark Summers et al.

It is certified that error appears in the above-identified patent and that said Letters Patent is hereby corrected as shown below:

Friday Time One
Friday Time Two

Appointment duration
Sales Representative:
Receive appointment reminder- Yes / No
Physician Description
Practice Description
Practice web site address

Exhibit 2
Patient Information
First name
Last name
D.O.B.
Daytime Phone
Evening Phone
Cell Phone
FAX
Address
City
State
ZIP/Postal code
SSN
email address

Insurance Information
Company
Insurance Co. Address:
Insurance Co. ZIP
Insurance Co. Phone
Employer
Policy Number
Group Number
HMO/PPO

Primary Care Physician
First name
Last name
Clinic Name

UNITED STATES PATENT AND TRADEMARK OFFICE
CERTIFICATE OF CORRECTION

PATENT NO. : 7,499,866 B2
APPLICATION NO. : 10/440594
DATED : March 3, 2009
INVENTOR(S) : Mark Summers et al.

It is certified that error appears in the above-identified patent and that said Letters Patent is hereby corrected as shown below:

City
State

Caller Information if Not Patient (spouse, friend, etc.)
First Name
Last Name
Phone
email address

Exhibit 3
Not Ready
Appointment Rescheduled
Treatment Discontinued
Insurance No Coverage
No Show
Problem no longer exists

Exhibit 4
Physician needs to reschedule
Physician cancelled appointment
Patient requested reschedule
Patient requested cancellation
Comments Signed and Sealed this Seventh Day of July, 2009

JOHN DOLL
*Acting Director of the United States Patent and Trademark Office*